United States Patent [19]

Mihara et al.

[11] Patent Number: 5,009,987
[45] Date of Patent: Apr. 23, 1991

[54] OPTICAL RECORDING MEDIUM CONTAINING IR-RAY ABSORPTIVE COMPOUND

[75] Inventors: Chieko Mihara, Tokyo; Tsuyoshi Santoh, Yokohama; Hiroyuki Sugata, Yamato; Tetsuro Fukui, Kawasaki, all of Japan

[73] Assignee: Canon Kabushiki Kaisha, Tokyo, Japan

[21] Appl. No.: 436,041

[22] Filed: Nov. 14, 1989

[30] Foreign Application Priority Data

Nov. 16, 1988 [JP] Japan .................. 63-287611
Nov. 16, 1988 [JP] Japan .................. 63-287612

[51] Int. Cl.$^5$ .................. G03C 1/00; G03C 1/492; B32B 3/02; G01D 9/00
[52] U.S. Cl. .................. 430/495; 430/270; 430/945; 346/135.1; 428/64
[58] Field of Search .............. 430/495, 945, 270, 512; 346/135.1

[56] References Cited

U.S. PATENT DOCUMENTS

| 3,251,881 | 5/1966 | Susi et al. | 260/576 |
| 3,484,467 | 12/1969 | Susi et al. | 260/440 |
| 3,575,871 | 4/1971 | Susi et al. | 252/300 |
| 4,540,649 | 9/1985 | Sakurai | 430/270 |
| 4,656,121 | 4/1987 | Sato et al. | 430/495 |

FOREIGN PATENT DOCUMENTS 85294162 3/1984 Japan .................. 430/495
69991 10/1986 Japan .

Primary Examiner—Paul R. Michl
Assistant Examiner—Ashley I. Pezzner
Attorney, Agent, or Firm—Fitzpatrick, Cella, Harper & Scinto

[57] ABSTRACT

The present invention relates to an optical recording medium comprising at least one of the following IR-ray absorptive compounds:

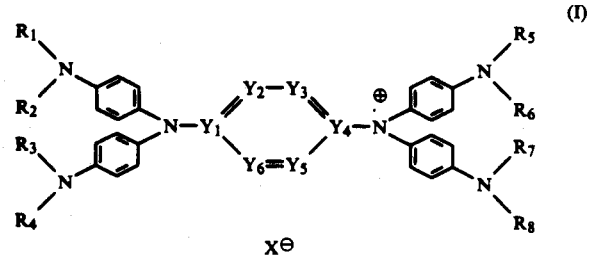

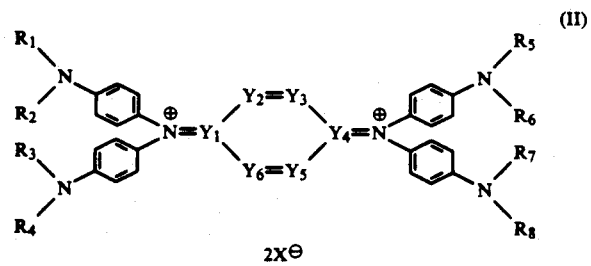

Incorporation of the IR-ray absorptive compound of the present invention into an optical recording medium noticeably improves the durability of the medium measured by repeated reproduction and light resistance.

5 Claims, No Drawings

OPTICAL RECORDING MEDIUM CONTAINING IR-RAY ABSORPTIVE COMPOUND

BACKGROUND OF THE INVENTION

1. Field of the Invention

The present invention relates to an IR-ray absorptive compound and an optical recording medium utilizing the same.

In particular, the present invention pertains to an IR-ray absorptive compound and an optical recording medium with improved durability as evidenced by repeated information reproduction and light resistance. The present invention can be utilized in optical discs or optical cards.

2. Related Background Art

Generally speaking, optical recording media, for instance, an optical disc or an optical card record high density information by forming optically detectable small pits of, for example, 1 μm on a thin recording layer provided on a substrate having a spiral, circular or linear groove thereon.

By scanning a laser beam which converges on the surface of the recording layer, the recording layer absorbs the laser energy and forms optically detectable pits, whereby information is written.

According to a heat mode recording system, the recording layer absorbs heat energy and forms a small pit (a concave portion) by evaporation or melting at that site. By using an organic dye thin film as the recording layer having high reflectance, the optical contrast of the recording pit can be set at a high level. For example, when a polymethine type dye, azulene type dye, cyanine type or pyrylium type dye, etc. with great light absorption relative to laser beam is used for an organic dye thin film, a light absorptive reflective film exhibiting metallic luster (i.e., reflectance on the order of 10 to 50%) can be obtained, providing an optical recording medium capable of laser recording and reflective reading. Particularly, when semiconductor laser with an oscillation wave length of 600 to 800 nm is used as the laser light source, there are further advantages in that the device can be made even smaller in size and lower in cost. However, organic dye thin films had the problems that recording and reproduction characteristics and storage stability may be lowered, because they deteriorate generally by the action of heat and light, etc.

To cope with such problems, U.S. Pat. No. 4,656,121 proposed a method to improve light resistance by incorporating an aminium salt or diimonium salt of a triarylamine type compound incorporated in a polymethine type dye.

SUMMARY OF THE INVENTION

An object of the present invention is to provide an IR-ray absorptive compound with improved light resistance and repeated reproduction durability, and which is better in solvent solubility when compared to those of the prior art.

Another object of the present invention is to provide an optical recording medium with improved light resistance and repeated reproduction durability as compared to the prior art which absorbs good productivity.

More specifically, the IR-ray absorptive compound of the present invention is represented by the following formula (I) or (II):

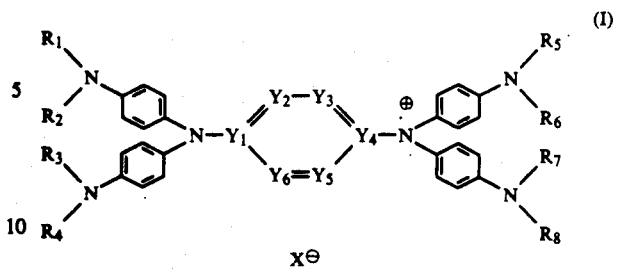

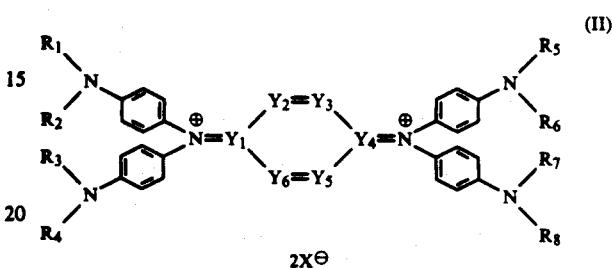

where $Y_1$, $Y_2$, $Y_3$, $Y_4$, $Y_5$, and $Y_6$ form a substituted or unsubstituted heterocycle which has at least one nitrogen atom; $R_1$ to $R_8$ are respectively a hydrogen atom, a halogen atom, or a univalent organic radical, or otherwise at least one of the combinations of the atomic groups of $R_1$ and $R_2$, $R_3$ and $R_4$, $R_5$ and $R_6$, and $R_7$ and $R_8$ forms together with the nitrogen a substituted or unsubstituted five-, six- or seven-membered heterocycle; the $R_1$ to $R_8$ being the same or different; the combinations of $R_1$ and $R_2$, $R_3$ and $R_4$, $R_5$ and $R_6$, and $R_7$ and $R_8$ being the same or different; and $X^\ominus$ is an anion.

The optical recording medium of the present invention contains at least one of the IR-ray absorptive compounds represented by the following formula (I) or (II).

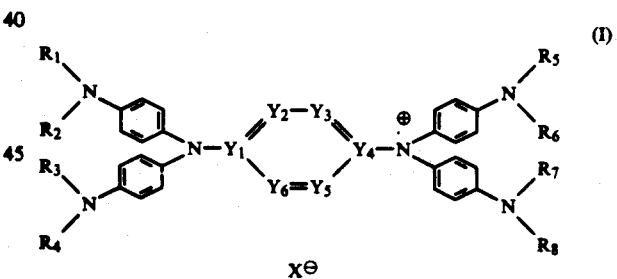

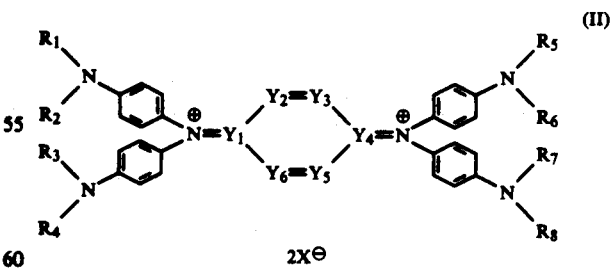

where $Y_1$, $Y_2$, $Y_3$, $Y_4$, $Y_5$, and $Y_6$ form a substituted or unsubstituted heterocycle which has at least one nitrogen atom; $R_1$ to $R_8$ are respectively a hydrogen atom, a halogen atom, or a univalent organic radical, or otherwise at least one of the combinations of the atomic groups of $R_1$ and $R_2$, $R_3$ and $R_4$, $R_5$ and $R_6$, and $R_7$ and $R_8$ forms together with the nitrogen a substituted or unsubstituted five-, six- or seven-memberd heterocycle; the $R_1$ to $R_8$ being the same or different; the combinations of $R_1$ and $R_2$, $R_3$ and $R_4$, $R_5$ and $R_6$, and $R_7$ and $R_8$ being the same or different; and $X^{\ominus}$ is an anion.

DETAILED DESCRIPTION OF THE PREFERRED EMBODIMENTS

The highly stable IR-ray absorptive compounds of the present invention resulted from molecular design work designed to increase the fraction of nitrogen atoms in known IR-ray absorptive compounds. Applicants undertook this work based on their discovery that, among coloring matter for optical recording such as triphenylmethane dyes and phthalocyanine dyes, those materials containing more nitrogen atoms generally tend to have higher stability.

The present invention is described in detail below.

The present invention relates to an IR-ray absorptive compound represented by the general formulae (I) or (II) below, and an optical recording medium containing in the recording layer at least one of the IR-ray absorptive compounds represented by the general formulae (I) or (II):

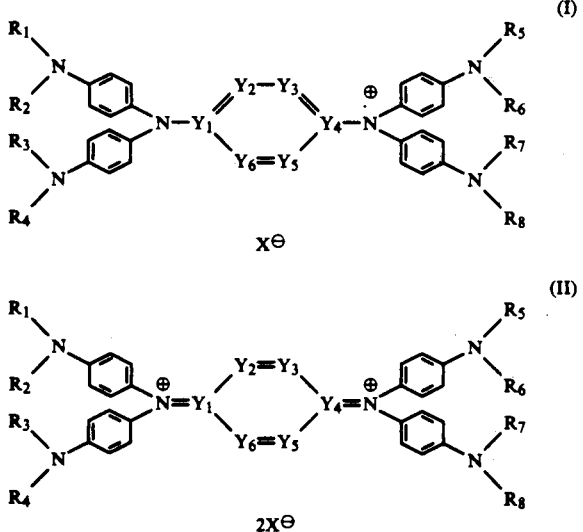

where $Y_1$, $Y_2$, $Y_3$, $Y_4$, $Y_5$, and $Y_6$ form a substituted or unsubstituted heterocycle which has at least one nitrogen atom; $R_1$ to $R_8$ are hydrogen atom, a halogen atom, or a univalent organic radical, or otherwise at least one of the combinations of the atomic groups of $R_1$ and $R_2$, $R_3$ and $R_4$, and $R_5$ and $R_6$, and $R_7$ and $R_8$ forms together with the nitrogen a substituted or unsubstituted five-, six- or seven-memberd heterocycle; the $R_1$ to $R_8$ being the same or different; the combinations of $R_1$ and $R_2$, $R_3$ and $R_4$, $R_5$ and $R_6$, and $R_7$ and $R_8$ being the same or different; and $X^{\ominus}$ is an anion.

In the general formulas (I) and (II), $R_1$ to $R_8$ includes hydrogen; a halogen such as fluorine, chlorine, bromine, and iodine; and a univalent organic radical such as a substituted or unsubstituted alkyl, a substituted or unsubstituted alkoxy, a substituted or unsubstituted alkoxyalkyl, a substituted or unsubstituted alkenyl, a substituted or unsubstituted alkynyl, and a substituted or unsubstituted aralkyl.

Particularly preferable are univalent organic radicals having 1–8 carbon atoms such as methyl, ehtyl, n-propyl, isopropyl, n-butyl, isobutyl, t-butyl, n-amyl, t-amyl, n-hexyl, n-octyl, t-octyl, etc., and other substituted alkyl radicals such as 2-hydroxyethyl, 3-hydroxypropyl, 4-hydroxybutyl, 2-acetoxyethyl, carboxymethyl, 2-carboxyethyl, 3-carboxypropyl, etc.

The alkoxyalkyl radicals include linear or branched alkoxyalkyls such as methoxymethyl, 2-methoxyethyl, 3-methoxypropyl, 2-methoxypropyl, 4-methoxybutyl, 3-methoxybutyl, 2-methoxybutyl, 5-methoxypentyl, 4-methoxypentyl, 3-methoxypentyl, 2-methoxypentyl, 6-methoxyhexyl, ethoxymethyl, 2-ethoxyethyl, 3-ethoxypropyl, 2-ethoxypropyl, 4-ethyoxybutyl, 3-ethoxybutyl, 5-ethoxypentyl, 4ethoxypentyl, 6-ethoxyhexyl, propoxymethyl, 2-propoxyethyl, 3-propoxypropyl, 4-propoxybutyl, 5-propoxypentyl, etc.

The alkoxy radicals include methoxy, ethoxy, propoxy, butoxy, etc. The alkenyl radicals include vinyl, propenyl, butenyl, pentenyl, hexenyl, heptenyl, octenyl, etc.

The aralkyl radicals include benzyl, p-chlorobenzyl, p-methylbenzyl, 2-phenylmethyl, 2-phenylpropyl, 3-phenylpropyl, α-naphtylemethyl, β-naphthylethyl, etc.

The alkynyl radicals include propargyl, butynyl, pentynyl, hexynyl, etc.

In particular, alkoxyalkyl radicals, alkenyl radicals, or alkynyl radicals give IR-ray absorptive compounds having an excellent solubility in a solvent.

The substituted or unsubstituted five-membered ring formed by at least one of the combinations of $R_1$ and $R_2$, $R_3$ and $R_4$, $R_5$ and $R_6$, and $R_7$ and $R_8$, together with the nitrogen includes a pyrrolidine ring, etc.; the substituted or unsubstituted six-membered ring includes piperidine, morpholine, tetrahydropyridine rings, etc.; and the substituted or unsubstituted seven-membered ring formed thereby includes a hexamethyleneimine ring, etc. The respective combinations may be the same or different. The formation of the ring from $R_n$ and $R_{n+1}$ (n is 1, 3, 5, or 7) provides IR-ray absorptive compounds which exhibit an enchanced stabilizing effect.

$X^{\ominus}$ represents anions including chloride, bromide, iodide, perchlorate, nitrate, benzenesulfonate, p-toluenesulfonate, methylsulfate, ethylsulfate, propylsulfate, tetrafluoroborate, tetraphenylborate, hexafluorophosphate, benzenesulfinate, acetate, trifluoroacetate, propionate, benzoate, oxalate, succinate, malonate, oleate, stearate, citrate, hydrogenphosphate, dihydrogenphosphate, pentachlorostannate, chlorosulfonate, fluorosulfonate, trifluoromethansulfonate, hexafluoroarsenate, hexafluoroantimonate, molybdate, tungstate, titanate, and zirconate, etc.

At least one of $Y_1$ to $Y_6$ is nitrogen, and the six atoms of $Y_1$ to $Y_6$ form a heterocycle such as

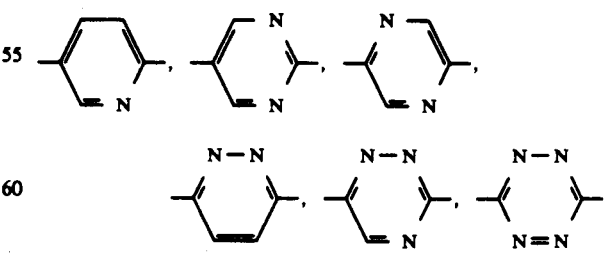

Which may be substituted by a lower alkyl lower alkoxy halogen or hydroxyl radicals.

The IR-ray absorptive compound of the present invention may be manufactured according to methods described in U.S. Pat. Nos. 3,251,881, 3,575,871 and, 3,484,467, and Japanese Patent Application Laid-open No. 61-69991 (1986). For example, one suitable process is shown below:

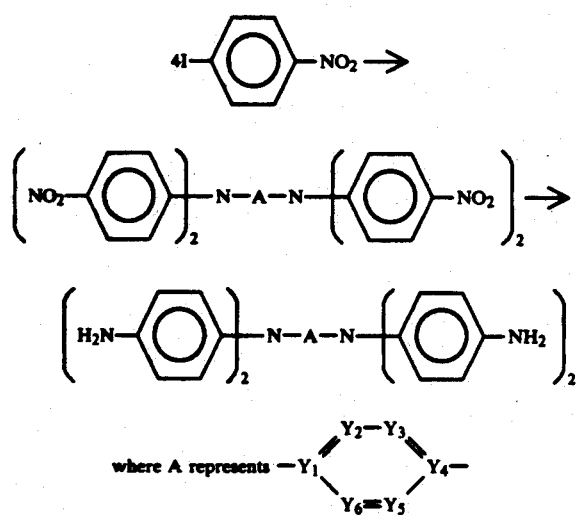

The amine prepared by the above Ullmann and reducing reactions is alkylated by selective substitution, and is then oxidized to give the final product.

In this alkylation reaction, pyrrolidine, piperidine, morpholine, or tetrahydropyridine rings may be provided using a suitable alkylating agent.

In the case where $R_1$ to $R_8$ are not symmetrical, the alkylation procedure must be conducted in multiple steps. Accordingly, from the standpoint of manufacturing cost, $R_1$ to $R_8$ are preferably to be the same.

As the five-membered ring, for example, a pyrrolidine ring can be formed by alkylation with 1,4-dibromobutane, 1,4-dichlorobutane, 1,4-diiodobutane, or the like. As the six-membered ring, a piperidine ring can be formed by using 1,5-dibromopentane, 1,5-dichloropentane, 1,5-diiodopentane or the like. A morpholine ring can be formed by hydroxyethylation with 2-bromoethanol, etc. and subsequent dehydration with acid treatment. A tetrahydropyridine ring can be formed by methacrylation with methacryl bromide and a subsequent acid treatment. A hexamethyleneimine ring can be formed by cyclization with 1,6-dibromohexane or the like.

The specific examples of the IR-ray absorptive compounds represented by the general formulas (I) and (II) of the present invention are shown below. For simplification, the compounds are shown in a form of X, $(Y_1Y_2Y_3Y_4Y_5Y_6)$, $(R_1R_2)(R_3R_4)(R_5R_6)(R_7R_8)$.

For example, in Formula (I), if $X^\ominus$ is $ClO_4^\ominus$, $Y_1$ to $Y_6$ from

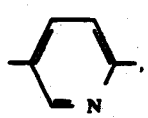

and $R_1$ to $R_8$ form a morpholine ring, the compound is simply shown as $ClO_4$, (CCCCNC),(CH$_2$CH$_2$OCH$_2$CH$_2$)$_4$.
Compound No.

(I)—1 ClO$_4$, (CCCCNC), (n-C$_3$H$_7$ n-C$_3$H$_7$)$_4$
(I)—2 ClO$_4$, (CCCCNC), (t-C$_4$H$_9$ t-C$_4$H$_9$)$_4$
(I)—3 SbF$_6$, (CCNCNC), (C$_2$H$_5$ C$_2$H$_5$)$_4$
(I)—4 SbF$_6$, (CCNCNC), (CH$_2$CH$_2$OCH$_3$ CH$_2$CH$_2$OCH$_3$)$_4$ (I) — 5 I, (CNNCNN), (CH$_2$C$\overset{CH_3}{=}$CH$_2$CH$_2$C$\overset{CH_3}{=}$CH$_2$)$_4$ (I)—6 ClO$_4$, (CCNCNC), (CH$_2$CH=CH$_2$ CH$_2$CH=CH$_2$)$_4$
(I)—7 Br, (CCCCNC), (iso-C$_3$H$_7$ iso-C$_3$H$_7$)$_4$
(I)—8 AsF$_6$, (CNCCNC), (n-C$_4$H$_9$ n-C$_4$H$_9$)$_3$(C$_4$H$_9$ CH$_2$CH=CH$_2$)
(I)—9 BF$_4$, (CCCCNC), (n-C$_8$H$_{17}$ n-C$_8$H$_{17}$)(OCH$_3$ OCH$_3$)$_3$
(I)—10 ClO$_4$, (CNCCNC), (CH$_2$C≡CH CH$_2$C≡CH)$_4$ (I) — 11 AsF$_6$, (CCNCNC), (n-C$_3$H$_7$n-C$_3$H$_7$)$_3$(C$_3$H$_7$C$_2$H$_4$C$\overset{CH_3}{=}$CH$_2$)

(I) — 12 CH$_3$——SO$_3$, (CCCCNC), (CH$_2$—C$_6$H$_4$—ClCH$_2$—C$_6$H$_4$—Cl)$_4$ (I) — 13 BF$_4$, (CNNCCC), (C$_3$H$_6$$\overset{CH_3}{\underset{|}{C}}$HCH$_3$C$_3$H$_6$$\overset{CH_3}{\underset{|}{C}}$HCH$_3$)$_4$ (I)—14 ClO$_4$, (CCNCNC), (C$_2$H$_5$ C$_2$H$_5$)$_4$
Compound No.
(I)—15 ClO$_4$, (CCCCNC), (CH$_2$CH$_2$CH$_2$CH$_2$)$_4$
(I)—16 BF$_4$, (CCCCNC), (CH$_2$CH$_2$OCH$_2$CH$_2$)$_4$ (I) — 17 ClO$_4$, (CCCCNC), ($\overset{CH_3}{\underset{|}{C}}$HCH$_2$CH$_2$CH$_2$)$_4$ (I)—18 AsF$_6$, (CCNCNC), (C$_3$H$_7$ C$_3$H$_7$)$_3$(CH$_2$CH$_2$CH$_2$)
(I)—19 SbF$_6$, (CCNCNC), (CH$_2$CH=CHCH$_2$)$_4$
(I)—20 Br, (CNNCNN), (CH$_2$CH$_2$CH$_2$CH$_2$CH$_2$)$_4$ (I) — 21 SbF$_6$, (CCNCNC), ($\overset{CH_3}{\underset{|}{C}}$HCH$_2$CH$_2$CH$_2$)$_4$ (I) — 22 I, (CCCCNC), ($\overset{CH_3}{\underset{|}{C}}$HCH$_2$CH$_2$CH$_2$)$_3$(CH$_2$CH$_2$CH$_2$CH$_2$)

(I)—23 ClO$_4$, (CCCCNC), (CH=C(CH$_3$)CH$_2$C(CH$_3$)$_2$CH$_2$)$_4$
(I)—24 CF$_3$SO$_4$, (CCNCNC), (CH$_2$CH$_2$CH$_2$CH$_2$CH$_2$CH$_2$)$_4$
(I)—25 SbF$_6$, (CNCCNC), (t-C$_4$H$_9$ t-C$_4$H$_9$)$_3$(CH$_2$CH$_2$=CH$_2$CH$_2$)
(I)—26 ClO$_4$, (CCCCNC), (CH$_2$CH$_2$OCH$_2$CH$_2$)$_4$ (I) — 27 SbF$_6$, (CCNCNC), ($\overset{CH_3}{\underset{|}{C}}$HCH$_2$CH$_2$$\overset{CH_3}{\underset{|}{C}}$H)$_4$ (I) — 28 ClO$_4$, (CCNCNC), ($\overset{CH_3}{\underset{|}{C}}$HCH$_2$CH$_2$CH$_2$)$_4$ Compound No.
(II)—1 ClO4, (CCCCNC), (n-C3H7 n-C3H7)4
(II)—2 ClO4, (CCCCNC), (t-C4H9 t-C4H9)4

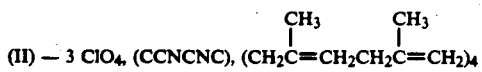
(II) — 3 ClO4, (CCNCNC), (CH2C=CH2CH2C=CH2)4 (with CH3 groups)

(II)—4 I, (CNNCCC), (C5H11 C5H11)4
(II)—5 Br, (CNNCNN), (OC2H5 OC2H5)4
(II)—6 ClO4, (CCNCNC), (CH2OC2H5 CH2OC2H5)4
(II)—7 AsF6, (CNCCNC), (CH2C=C3H7 CH2C=C3H7)4
(II)—8 ClO4, (CCCCNC), (CH2C6H5 CH2C6H5)(C2H5 C2H5)3
(II)—9 SbF6, (CCNCNC), (CH2OCH2OCH3 CH2OCH2OCH3)4
(II)—10 BF4, (CNNCNN), (C6H13 C6H13)3(C6H13 C5H10Cl)

(II) — 11 ClO4, (CCCCNC), (CH2CHCH3CH2CHCH3)4 (with CH3 groups)

(II)—12 BF4, (CNCCNC), (iso-C3H7iso-C3H7)3(C2H5 C2H5)
(II)—13 AsF6, (CCNCNC), (CH2CH2OCH3 CH2CH2OCH3)4
Compound No.
(II)—14 ClO4, (CCCCNC), (CH2CH2CH2CH2)4
(II)—15 ClO4, (CCCCNC), (CH2CH2OCH2CH2)4

(II) — 16 ClO4, (CCCCNC), (CHCH2CH2CH2)4 (with CH3 group)

(II)—17 Br, (CNCCNC), (C4H9 C4H9)3(CH2CH2CH2CH2CH2CH2)
(II)—18 AsF6, (CNNCNN), (OCH3 OCH3)3(CH2CH2CH2CH2)
(II)—19 SbF6, (CCNCNC), (CH=C(CH3)CH2C(CH3)2CH2)4
(II)—20 I, (CCCCNC), (t-C4H9 t-C4H9)3(CH2CH2OCH2CH2)

(II) — 21 SbF6, (CCNCNC), (CHCH2CH2CH)4 (with CH3 CH3 groups)

(II)—22 ClO4, (CCCCNC), (CH=C(CH3)CH2C(CH3)2CH2)4
(II)—23 ClO4, (CNCCNC), (CH2CH=CHCH2)4
(II)—24 NO3, (CNCCNC), (CH2CH2CH2CH2CH2CH2)4

(II) — 25 AsF6, (CCNCNC), (CHCH2CH2CH2CH2)4 (with CH3 group)

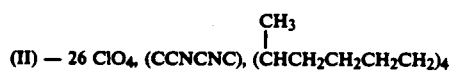
(II) — 26 ClO4, (CCNCNC), (CHCH2CH2CH2CH2)4 (with CH3 group)

(II)—27 SbF6, (CCNCNC), (CH2CH=CHCH2)4

The IR-ray absorptive compounds composed of the above-described aminium or diimonium salt have their maximum abosrption at a wavelength longer than 900 nm, and an absorption coefficient of the absorption peak as high as several hundred thousands.

Such IR-ray absorptive compounds are useful also for heat insulation films, sunglasses and the like, in addition to the use for the material of optical recording mediums. Incorporation of the IR-ray absorptive compounds of the present invention to an optical recording medium gives high heat stability and light resistance to the medium. Although one IR-ray absorptive compound may be incorporated by itself into a recording layer, it is preferable to also incorporate additional IR-ray absorptive coloring matters for optical recording in order to optimally raise the sensitivity and reflectivity of the recording layer.

The near infrared light absorbing coloring matter which may also be used to form a recording layer of an optical recording medium may be any of generally known coloring matters, such as cyanine, merocyanine, chroconium, squarium, azulenium, polymethine, naphthoquinone, pyrylium and, phthalocyanine type coloring matters, etc.

In comparison with such coloring matters, the amount of addition of the IR-ray absorptive compound composed of the aminium salt of the general formula (I) or the diimonium salt of the general formula (II) is, based on the solid matter, in the range of from 1 to 60% by weight, preferably 5 to 40% by weight, more preferably 10 to 30% by weight, of the recording layer.

In addition to these compounds, a binder may be incorporated in the recording layer. The binders include cellulose esters such as nitrocellulose, cellulose phosphate, cellulose sulfate, cellulose acetate, cellulose propionate, cellulose butyrate, cellulose myristate, cellulose palmitate, cellulose acetate propionate, cellulose acetate butyrate, etc.; cellulose ethers such as methylcellulose, ethylcellulose, propylcellulose, butylcellulose, etc.; vinyl resins such as polystyrene, polyvinyl chloride, polyvinyl acetate, polyvinylbutyral, polyvinylacetal, polyvinyl alcohol, polyvinylpyrrolidone, etc.; copolymer resins such as a styrene-butadiene copolymer, a styrene-acrylonitrile copolymer, a styrene-butadiene-acrylonitrile copolymer, a vinyl chloride-vinyl acetate copolymer, etc.; acrylic resins such as polymethyl methacrylate, polymethyl acrylate, polybutyl acrylate, polyacrylic acid, polymethacrylic acid, polyacrylamide, polyacrylonitrile, etc.; polyesters such as polyethylene terephthalate; polyarylate resins such as poly(4,4'-isopropylidenediphenylene-co-1,4-cyclochexylenedimethylene carbonate), poly(ethylenedioxy-3,3'-phenylene thiocarbonate), poly(4,4'-isopropylidenediphenylene carbonate-coterephthalate), poly(4,4'-isopropylidenediphenylene carbonate), poly(4,4'-sec-butylidenediphenylene carbonate, poly(4,4-isopropylidenediphenylene carbonate-block-oxyethylene), etc.; polyamides, polyimides, epoxy resins, phenol resins; and polyolefins such as polyethylene, polypropylene, chlorinated polyethylene, etc.

Into the recording layer, there may be added surfactants, antistatic agents, stabilizers, dispersion-type fire retardants, slipping agents, plasticizers, etc.

A subbing layer may be provided between a recording layer and a substrate. A protective layer may be provided on a recording layer.

The subbing layer is provided to impart solvent resistance, and improve reflectivity, and repetitive reproducibility. The protective layer is provided to protect the recording layer from scratches, dust, and dirt, and to impart environmental stability to the recording layer.

The materials mainly used for this purpose are inorganic compounds, metals, or organic high-molecular weight compounds. The inorganic compounds includes $SiO_2$, $MgF_2$, SiO, $TiO_2$, ZnO, TiN, SiN, etc. The metals include Zn, Cu, Ni, Al, Cr, Ge, Se, Cd, etc. The organic high-molecular weight compounds include ionomer resins, polyamide resins, vinyl resins, natural high polymers, epoxy resins, silane coupling agents, etc.

In the present invention, the recording layer may comprise not only a layer for information recording but also, a reflective layer for light reflection.

The materials for the substrates include plastics such as polyesters, polycarbonates, acrylic resins, polyolefin resins, phenol resins, epoxy resins, polyamides, polyimides, etc.; glass and metals.

The organic solvent for coating is selected depending on the desired state of dispersion or dissolution. Generally the solvents which are used include alcohols such as methanol, ethanol, isopropanol, diacetone alcohol, etc.; ketones such as acetone, methyl ethyl ketone, cyclohexanone, etc.; amides such as N,N-dimethylformamide, N,N-dimethylacetamide, etc.; sulfoxides such as dimethylsulfoxide, etc.; ethers such as tetrahydrofuran, dioxane, ethyleneglycol monomethyl ether, etc.; esters such as methyl acetate, ethyl acetate, butyl acetate, etc.; aliphatic halogenated hydrocarbons such as chloroform, methylene chloride, dichloroethylene, carbon tetrachloride, trichloroethylene, etc.; aromatic hydrocarbons such as benzene, toluene, xylene, monochlorobenzene, dichlorobenzene, etc.; aliphatic hydrocarbons such as n-hexa cyclohexanoligroin, etc.

The coating may be carried out by the use of coating method such as dip coating, spray coating, spinner coating, bead coating, Mayer bar coating, blade coating, roller coating or curtain coating. The layer thickness of the recording layer formed by using such solvent is 50Å-100 μm, preferably 200 Å-1 μm.

As described above, the IR-ray absorptive compounds of the present invention represented by the general formula (I) and the general formula (II) have a large absorption in the infrared region, and can be easily synthesized.

Incorporation of the IR-ray absorptive compound of the present invention into an optical recording medium noticeably improves durability as measured by repeated reproduction and light resistance.

The examples below are intended to illustrate specifically the present invention.

SYNTHESIS EXAMPLE 1

Into a solution of 15 parts by weight of 2-amino-5-nitropyridine in 120 parts of 2N aqueous hydrogen chloride, 14 parts of powdery tin was added with stirring, and stirred further for 2 hours. After the reaction, the mixture was poured into 600 parts by weight of ice water, and was neutralized with aqueous sodium hydroxide solution to obtain the intended 2,5-diaminopyridine.

0.1 mole of 2,5-diaminopyridine, 0.43 mole of p-nitrochlorobenzene, 0.23 mol of anhydrous potassium carbonate, and 2 parts by weight of powdery copper in 130 parts of dimethylformamide was refluxed with stirring for 4 days. After the reaction, the reaction mixture was filtered. The filtered matter was washed with dimethyformamide, water, and acetone, and was dried to obtain 26 parts of tetrakis(p-nitrophenyl)-2,5-diaminopyridine.

24 parts of the compound prepared above together with 95 parts of dimethylformamide and 2 parts of palladium-carbon, as a hydrogenation catalyst, were put into an autoclave, and the mixture was stirred at a temperature of 90°-100° C. with supply of hydrogen at a pressure of 5.0 kg/cm$^2$ until hydrogen absorption ceased.

The reaction mixture was filtered and the separated solid matter was washed with dimethylformamide. The filtrate was poured into 330 parts of ice water. After stirring for some time, the precipitate was collected by filtration. It was crystallized from an ethanol-dimethyformamide mixed solution to obtain 10 parts of tetrakis(p-aminophenyl)2,5-diaminopyridine. The purity was 98.7% according to high speed liquid chromatography.

Synthesis of Compound No. I-2

3 parts of the above described amino compound together with 18 parts of dimethylformamide, 0.7 part of anhydrous sodium hydrogencarbonate, and 3.9 parts of t-butyl bromide was heated and stirred at 100° C.-130° C. After 36 hours of reaction, the reaction mixture was poured into 100 part of ice water, and the mixture was extracted with ethyl acetate. The extract was dried, and purified by employing a silica gel column. The yield of the product was 3.5 parts. The NH stretching vibration of the amino group was confirmed to have disappeared according to IR absorption analysis.

One part of this compound was dispersed in 20 parts of acetone, and equivalent moles of silver perchlorate were added thereto with stirring. After reaction for 1 hour at a room temperature, the deposited silver was filtered off. The filtrate was diluted with isopropyl ether, and left standing. The deposited crystalline matter was collected by filtration. The yield was 0.8 part.

The compound No. I-2 thus synthesized had a large absorption band at an infrared region with the maximum absorption wavelength of 1110 nm, and absorption coefficient of 38,000.

Synthesis of Compound No. I-17

3 parts of the above described amino compound together with 18 parts of dimethylformamide, 0.5 part of anhydrous sodium hydrogencarbonate, and 2.5 parts of 1,4-dibromopentane was heated and stirred at 100° C.-130° C. After 36 hours of reaction, the reaction mixture was poured into 100 part of ice water, and the mixture was extracted with ethyl acetate. The extract was dried, and purified by employing a silica gel column. The yield of the product was 3.5 parts. The NH stretching vibration of the amino group was confirmed to have disappeared according to IR absorption analysis.

One part of this compound was dispersed in 20 parts of acetone, and equivalent moles of silver perchlorate were added thereto with stirring. After reaction for 1 hour at a room temperature, the deposited silver was filtered off. The filtrate was diluted with isopropyl ether, and left standing. The deposited crystalline matter was collected by filtration. The yield was 0.9 part.

The compound No. I-17 thus synthesized had a large absorption band at an infrared region with the maximum absorption wave length of 1119 nm, and absorption coefficient of 62,000.

Synthesis of Compound No. II-2

One part of the tetrakis(p-dibutylaminophenyl)-2,5-diaminopyridine used in the synthesis of Compound No. I-2 was dispersed in 20 parts of acetone, and two twofold moles of silver perchlorate was added thereto with stirring. After reaction for one hour at a room temperature, the deposited silver was filtered off. The filtrate was diluted with isopropyl ether. 0.60 part of deposited crystalline matter was collected by filtration.

The description above is made regarding the compounds having perchlorate as the anion. If other anion is desired, the intended compound can be easily obtained by employing a silver salt of the corresponding anion. For example, silver salts such as $AgSbF_6$, $AgBF_4$, $Ag_2SO_4$, $AgNO_3$, $AgSO_3C_6H_4CH_3$, $AgSO_3CF_3$, etc. may be used. Otherwise, the compounds can be prepared by electrolytic oxidation.

Synthesis of Compound No. II-16

One part of the pyrrolidine compound obtained in the course of the synthesis of Compound No. I-17 was dispersed in 20 parts of acetone, and thereto two times moles of silver perchlorate was added with stirring. After reaction for one hour at a room temperature, the deposited silver was filtered off. The filtrate was diluted with isopropyl ether. 0.57 part of deposited crystalline matter was collected by filtration.

The above description is made regarding compounds having perchlorate as the anion. If another anion is desired, the intended compound can, of course, be easily obtained by employing a silver salt of the corresponding anion. For example, silver salts such as $AgSbF_6$, $AgBF_4$, $Ag_2SO_4$, $AgNO_3$, $AgSO_3C_6H_4CH_3$, $AgSO_3CF_3$, etc. may be used. Otherwise, the compounds can be prepared by electrolytic oxidation.

SYNTHESIS EXAMPLE 2

Tetrakis(p-aminophenyl)-2,5-diaminopryrimidine was prepared in a yield of 23 parts in the same manner as in Synthesis example 1, except that 2-amino-5-nitropyrimidine was used in place of 2-amino-5-nitropyridine used in Synthesis example 1.

Synthesis of Compound No. I-4

4 parts of the amino compound obtained in Synthesis example 2 together with 24 parts of dimethylformamide, 1.0 part of anhydrous sodium hydrogencarbonate, and 4.0 parts of 2-ethoxyethyl bromide was heated and stired at 100° C.-130° C. After 36 hours of reaction, the reaction mixture was poured into 150 part of ice water, and the mixture was extracted with ethyl acetate. The extract was dried, and purified by employing a silica gel column. The yield of the product was 3.8 parts. The NH stretching vibration of the amino group was confirmed to have disappeared according to IR absorption analysis.

One part of this compound was dispersed in 20 parts of acetone, and thereto the equivalent moles of silver hexafluoroantimonate was added with stirring. After reaction for 1 hour at a room temperature, the deposited silver was filtered off. The filtrate was diluted with isopropyl ether, and left standing. The deposited crystalline matter was collected by filtration. The yield was 0.7 part. The maximum absorption wavelength was 1120 nm.

Synthesis of Compound No. I-19

3 parts of the amino compound obtained in Synthesis example 2 together with 18 parts of dimethylformamide, 0.6 part of anhydrous sodium hydrogencarbonate, and 4.0 parts of 1,4-dibromobutene was heated and stirred at 100° C.-130° C. After 36 hours of reaction, the reaction mixture was poured into 130 part of ice water, and the mixture was extracted with ethyl acetate. The extract was dried, and purified by employing a silica gel column. The yield of the product was 3.5 parts. The NH stretching vibration of the amino group was confirmed to have disappeared according to IR absorption analysis.

One part of this compound was dispersed in 20 parts of acetone, and thereto the equivalent moles of silver hexafluoroantimonate was added with stirring. After reaction for 1 hour at a room temperature, the deposited silver was filtered off. The filtrate was diluted with isopropyl ether, and left standing. The deposited crystalline matter was collected by filtration. The yield was 0.8 part. The maximum absorption wavelength was 1109 nm.

Synthesis of Compound No. II-13

0.5 part of tetrakis(p-diethoxymethylaminophenyl)-2,5-diaminopyridine which was obtained in the course of the synthesis of Compound No. I-4 was dispersed in 20 parts of acetone. Twofold the moles of silver perchlorate was added thereto with stirring, and stirring was continued for one hour. After the reaction, the deposited silver salt was filtered off and washed with acetone sufficiently. Acetone was evaported off from the filtrate. The residue was washed with water, and dried under a reduced pressure. The yield of the product was 0.40 part. The product was an IR-ray absorptive compound having a maximum absorption peak at the wavelength of 1180 nm.

Synthesis of Compound No. II-27

1.0 part of pyrroline compound which was obtained in the course of the synthesis of Compound No. I-19 was dispersed in 40 parts of acetone. Thereto the two times moles of silver perchlorate was added with stirring, and stirring was continued for one hour. After the reaction, the deposited silver salt was filtered off and washed with acetone sufficiently. The acetone was evaporated off from the filtrate. The residue was washed with water, and dried under a reduced pressure. The yield of the product was 0.60 part. The product was an IR-ray absorptive compound having the maximum absorption peak at the wavelength of 1060 nm.

The examples are described below in which the IR-ray absorptive compounds of the general formulas (I) and (II) are utilized as optical recording mediums.

EXAMPLE 1-1

On a substrate of 130 mm in diameter and 1.2 mm in thickness made of polymethyl methacrylate (hereinafter referred to as PMMA), pregrooves of 50 μ were provided. Thereon a solution in which a polymethine dye (IR-820, made by Nippon Kayaku K. K.) and the above described IR-ray absorptive compound No. I-2 were dissolved in a weight ratio of 90:10 in dichloromethane was applied by spin coating to provide a 800-Å recording layer. The medium thus prepared was sticked together with other PMMA substrate with insertion of 0.3 mm spacers at the inner periphery side and the outer periphery side by use of an ultraviolet-curing resin adhesive to give an optical recording medium of air-sandwich structure.

EXAMPLE 1-2

An optical recording medium was prepared in the same manner as in Example 1-1 except that the IR-ray absorptive compound No. I-17 was used in place of Compound No. I-2.

The optical recording mediums prepared in the above Examples 1-1 and 1-2 were subjected to tests as below. The writing was conducted on the optical recording medium rotating at a rate of 1800 rpm with a semiconductor laser of wavelength of 830 nm and with recording power of 6 mW and recording frequency of 3 MHz from the substrate side. Subsequently reproduction was conducted with a readout power of 0.8 mW, and the C/N ratio was measured by spectrum analysis. After 100 thousands times of readout, (namely, repetition of reproduction) was conducted, the C/N ratio was again measured.

Separately, the optical recording medium prepared as mentioned above, was exposed to xenon lamp light of 1 KW/m$^2$ for 100 hours to test the light stability. After the exposure the reflectivity and the C/N ratio were measured. The results are shown in Table 1.

TABLE 1

| Example No. | Initial Reflectivity (%) | Initial C/N (dB) | After repeated reproduction C/N (dB) | After light stability test Reflectivity (%) | After light stability test C/N (dB) |
|---|---|---|---|---|---|
| 1-1 | 24.7 | 57 | 54 | 22.6 | 54 |
| 1-2 | 25.1 | 58 | 57 | 22.9 | 55 |

EXAMPLE 2-1

Onto the same substrate as the one in Example 1-1, a recording layer was provided by the use of a solution containing 1-guaiazurenyl-5-(6'-t-butylazulenyl)-2,4-pentadienol perchlorate and the above mentioned IR-ray absorptive compound No. I-1 in a weight ratio of 90:10 in the same manner as in Example 1-1, thus preparing a recording medium.

EXAMPLE 2-2

An optical recording medium was prepared in the same manner as in Example 2-1 except that the IR-ray absorptive compound No. I-28 was used in place of Compound No. I-1.

The optical recording mediums prepared thus were subjected to the same tests as in Example 1. The results are shown in Table 2.

TABLE 2

| Example No. | Initial Reflectivity (%) | Initial C/N (dB) | After repeated reproduction C/N (dB) | After light stability test Reflectivity (%) | After light stability test C/N (dB) |
|---|---|---|---|---|---|
| 2-1 | 27.5 | 56 | 55 | 23.5 | 53 |
| 2-2 | 27.8 | 55 | 53 | 23.5 | 52 |

EXAMPLES 3-9

Optical recording mediums which contains the organic coloring matter and the IR-ray absorptive compound shown in Table 3 were prepared and tested in the same manner as in Example 1. The test results are shown in Table 4.

TABLE 3

| Example No. | Organic coloring matter (A) | IR-ray absorptive compound (B) | Ratio A/B by weight |
|---|---|---|---|
| 3-1 | 1,5-Diguaiazulenyl-2,4-pentadienium perchlorate | II-6 | 90:10 |
| 3-2 | | II-15 | 80:20 |
| 4-1 | (p-diethylaminophenyl)-(p-butylphenyl)methylene-1-cyclopenten-2-yl-3-(p-dimethylaminophenyl)-(p-ethoxyphenyl)carbonium perchlorate | I-6 | 85:15 |
| 4-2 | | I-15 | 90:10 |
| 5-1 | 1,5-bis(diethylaminophenyl)-1,5-diphenyl-2,4-pentadienium perchlorate | II-11 | 80:20 |
| 5-2 | | II-26 | 80:20 |
| 6-1 | 1,1'-dimethoxyethyl-3,3,3'3'-tetramethyl-2,2'-indotricarbocyanine perchlorate | I-4 | 85:15 |
| 6-2 | | I-28 | 85:15 |
| 7-1 | NK-1414 (made by Nippon Kanko Sikiso K. K.) | II-20 | 75:25 |
| 7-2 | | II-21 | 75:25 |
| 8 | 1-Guaiazulenyl-5,5-bis(Diethylaminophenyl)-2,4-pentadienol hexafluoroantimonate | I-2 and II-2 | 70:15:15 |
| 9 | IR-820 (made by Nippon Kayaku K. K.) | I-15 and II-14 | 80:10:10 |

COMPARATIVE EXAMPLES 1-6

Optical recording mediums were prepared and evaluated in the same manner as in Examples 1, 2, and 5 except that the IR-ray absorptive compounds in Examples 1-6 were not used. The results are shown in Table 4.

TABLE 4

| | Initial Reflectivity (%) | Initial C/N (dB) | After repeated reproduction C/N (dB) | After light stability test Reflectivity (%) | After light stability test C/N (dB) |
|---|---|---|---|---|---|
| Example No. | | | | | |
| 3-1 | 27.5 | 55 | 53 | 22.0 | 51 |
| 3-2 | 27.4 | 55 | 54 | 22.1 | 53 |
| 4-1 | 25.4 | 54 | 53 | 20.1 | 50 |
| 4-2 | 25.2 | 54 | 53 | 20.0 | 50 |
| 5-1 | 25.9 | 56 | 54 | 20.5 | 53 |
| 5-2 | 25.6 | 55 | 53 | 20.9 | 51 |
| 6-1 | 36.0 | 55 | 54 | 30.5 | 52 |
| 6-2 | 35.3 | 52 | 50 | 29.5 | 49 |
| 7-1 | 32.7 | 53 | 52 | 21.8 | 51 |
| 7-2 | 32.4 | 53 | 50 | 19.0 | 48 |
| 8 | 24.9 | 52 | 50 | 20.2 | 49 |
| 9 | 24.9 | 53 | 50 | 20.5 | 49 |
| Comparative example No. | | | | | |
| 1 | 19.9 | 50 | 46 | 13.4 | 33 |
| 2 | 28.4 | 55 | 52 | 15.2 | 34 |
| 3 | 27.7 | 56 | 51 | 14.2 | 35 |
| 4 | 25.6 | 55 | 49 | 13.9 | 31 |
| 5 | 25.8 | 54 | 49 | 13.7 | 31 |
| 6 | 37.1 | 56 | 48 | 9.8 | 29 |

EXAMPLES 10-14

Pregrooves are provided on a substrate having a wallet size of 85 mm in length, 54 mm in width, and 0.4 mm in thickness made of polycarbonate (hereinafter referred to as PC) according to a hot press method. Thereon a solution of an organic coloring matter shown in Table 5, and an IR-ray absorptive compound in diacetone alcohol was applied by using bar coating method, and dried to obtain a recording layer of 850 Å thick.

Onto the recording layer, a hot melt adhesive sheet of ethylene-vinyl acetate type was laminated. Further thereon a PC protective plate of an wallet size and 0.3 mm thick was superposed, and the superposed matter was allowed to pass through between a pair of rollers with a surface temperature maintained at 110° C., to prepare an optical card of closely contacted encapsulation type without an air gap.

The optical recording medium of each of the above Examples was mounted on a stage driven in X and Y directions. Onto the organic thin recording layer, information was written in from the 0.4-mm thick PC substrate side by employing a semiconductor laser of oscillation wavelength of 830 nm with recording power of 4.0 mW and recording pulse of 80 μsec in the direction of Y axis. The information was reproduced with a read-out power of 0.4 mW, and the contrast ratio (A-B)/A was measured (wherein A is the signal strength at non-recorded portion, and B is the signal strength at the recorded portion).

Separately the same optical recording mediums prepared under the above mentioned conditions were tested for light stability in the same manner as in Example 1. The reflectivity and the contrast ratio after the light exposure were measured. The results are shown in Table 6.

TABLE 5

| Example No. | Organic coloring matter (A) | IR-ray absorptive compound (B) | Ratio A/B by weight |
|---|---|---|---|
| 10-1 | IR-820 (Made by Nippon Kayaku K. K.) | II-2 | 85:15 |
| 10-2 |  | II-14 | 90:10 |
| 11-1 | (p-Dimethylaminophenyl)-(p-ethoxyphenyl)methylene- | I-14 | 90:10 |
| 11-2 | 1-cyclopenten-2-yl-3-(p-dimethylaminophenyl-(p-ethoxyphenyl)carbonium perchlorate | I-19 | 85:15 |
| 12-1 | 1,5-bis(dipropylaminophenyl)-1,5-diphenyl-2,4- | I-7 | 75:25 |
| 12-2 | pentadienium perchlorate | I-26 | 75:25 |
| 13 | IR-820 (Made by Nippon Kayaku K. K.) | I-2 | 70:30 |
| 14 | 1-Guaiazulenyl-5,5-bis(dimethyaminophenyl)-2,4-pentadienium perchlorate | II-16 | 85:15 |

COMPARATIVE EXAMPLES 7-10

Optical recording mediums were prepared and evaluated in the same manner as in Examples 9 and 11 except that the IR-ray absorptive compounds in Examples 10, 11, 12, and 14 were not used. The results are shown in Table 6.

TABLE 6

| Example No. | Initial | | After light stability test | |
|---|---|---|---|---|
|  | Reflectivity (%) | Contrast ratio | Reflectivity (%) | Contrast ratio |
| 10-1 | 14.8 | 0.74 | 12.8 | 0.70 |
| 10-2 | 14.8 | 0.76 | 12.8 | 0.71 |
| 11-1 | 15.4 | 0.73 | 13.4 | 0.69 |
| 11-2 | 15.5 | 0.73 | 13.6 | 0.69 |
| 12-1 | 15.2 | 0.70 | 13.2 | 0.67 |
| 12-2 | 15.3 | 0.74 | 13.6 | 0.68 |
| 13 | 15.0 | 0.73 | 12.9 | 0.68 |
| 14 | 15.7 | 0.79 | 10.2 | 0.62 |
| Comparative Example No. |  |  |  |  |
| 7 | 14.9 | 0.69 | 11.7 | 0.64 |
| 8 | 15.8 | 0.79 | 9.0 | 0.48 |
| 9 | 15.1 | 0.70 | 10.2 | 0.60 |
| 10 | 15.9 | 0.78 | 9.5 | 0.50 |

We claim:

1. An optical recording medium, comprising a recording layer containing at least one IR-ray absorptive compounds represented by formulae (I) or (II):

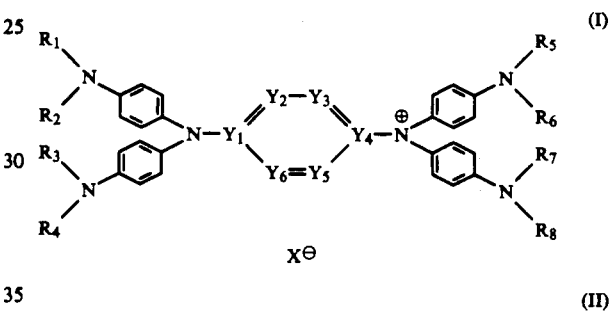

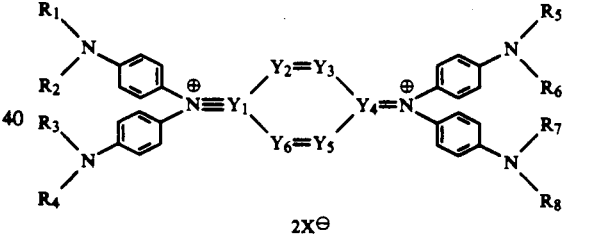

where $Y_1$, $Y_2$, $Y_3$, $Y_4$, $Y_5$, and $Y_6$ form a substituted or unsubstituted heterocycle which has at least one nitrogen atom; $R_1$ to $R_8$ are hydrogen, halogen, or a univalent organic radical, or at least one of the combinations of the atomic groups of $R_1$ and $R_2$, $R_3$ and $R_4$, $R_5$ and $R_6$, and $R_7$ and $R_8$ are the same or different; and $X^-$ is an anion.

2. An optical recording medium according to claim 1, wherein compound of formula (I) or (II) is contained in an amount of from 1 to 60% by weight based on the total solids in said recording layer.

3. An optical recording medium according to claim 2, wherein the compound of formula (I) or (II) is contained in an amount of from 5 to 40% by weight based on the total solids in said recording layer.

4. An optical recording medium according to claim 3, wherein the compound of formula (I) or (II) is contained in an amount of from 10 to 30% by weight based on the total solids in said recording layer.

5. An optical recording medium according to claim 1, further comprising a protective layer on said recording layer.

* * * * *

UNITED STATES PATENT AND TRADEMARK OFFICE
CERTIFICATE OF CORRECTION

PATENT NO. : 5,009,987
DATED : April 23, 1991
INVENTOR(S) : CHIEKO MIHARA, ET AL.

Page 1 of 2

It is certified that error appears in the above-identified patent and that said Letters Patent is hereby corrected as shown below:

COLUMN 1

Line 19, "record" should read --can record--.
    Line 30, "By using" should read --¶ By using--.

COLUMN 3

Line 48, "hydrogen" should read --a hydrogen--.
    Line 53, "memberd" should read --membered--.
    Line 66, "ehtyl," should read --ethyl,--.

COLUMN 4

Line 11, "4ethoxypentyl" should read --4-ethoxypentyl--.
    Line 68, "and," should read --and--.

COLUMN 5

Line 57, "Formula" should read --Formulae--.
    Line 58, "from" should read --form--.

COLUMN 6

Line 14, "$(n-C_4H_9\ n-C_4H_9)_3$" should read
          --$(n-C_4H_9\ n-C_4H_9)_3$--.

COLUMN 8

Line 12, "matters" should read --matter(s)--.
    Line 25, "formula" should read --formulae--.
    Line 63, "layer." should read --layer. The-- and
          delete new ¶.

UNITED STATES PATENT AND TRADEMARK OFFICE
CERTIFICATE OF CORRECTION

PATENT NO. : 5,009,987
DATED : April 23, 1991
INVENTOR(S) : CHIEKO MIHARA, ET AL.

It is certified that error appears in the above-identified patent and that said Letters Patent is hereby corrected as shown below:

COLUMN 10

Line 25, "100 part" should read --100 parts--.
Line 50, "100 part" should read --100 parts--.

COLUMN 16

Formula (II), "$\overset{\oplus}{N}\equiv Y_1$" should read --$\overset{\oplus}{N}=Y_1$--.
Line 54, "compound" should read --the compound--.

Signed and Sealed this

Twenty-ninth Day of December, 1992

Attest:

DOUGLAS B. COMER

Attesting Officer     Acting Commissioner of Patents and Trademarks